United States Patent
Ukil et al.

(10) Patent No.: US 12,038,949 B2
(45) Date of Patent: Jul. 16, 2024

(54) METHOD AND SYSTEM FOR CONTRADICTION AVOIDED LEARNING FOR MULTI-CLASS MULTI-LABEL CLASSIFICATION

(71) Applicant: Tata Consultancy Services Limited, Mumbai (IN)

(72) Inventors: Arijit Ukil, Kolkata (IN); Arpan Pal, Kolkata (IN); Soumadeep Saha, Kolkata (IN); Utpal Garain, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 0 days.

(21) Appl. No.: 18/383,930

(22) Filed: Oct. 26, 2023

(65) Prior Publication Data

US 2024/0143630 A1 May 2, 2024

(30) Foreign Application Priority Data

Nov. 1, 2022 (IN) .............................. 202221062230

(51) Int. Cl.
G06F 16/28 (2019.01)
(52) U.S. Cl.
CPC ................................. G06F 16/285 (2019.01)
(58) Field of Classification Search
CPC .......... G06N 20/00; G06N 3/08; G06N 5/025; G06F 18/2431; G06F 18/24765;

(Continued)

(56) References Cited

U.S. PATENT DOCUMENTS

2018/0336481 A1* 11/2018 Guttmann .............. G06N 5/022
2019/0392075 A1* 12/2019 Han ........................ G06F 16/285

(Continued)

OTHER PUBLICATIONS

Ghiassi et al., "TrustNet: Learning from Trusted Data Against (A)symmetric Label Noise," (2021), pp 52-62.

(Continued)

*Primary Examiner* — Robert W Beausoliel, Jr.
*Assistant Examiner* — Cheryl M Shechtman
(74) *Attorney, Agent, or Firm* — FINNEGAN, HENDERSON, FARABOW, GARRETT & DUNNER LLP

(57) ABSTRACT

This disclosure relates generally to multi-class multi-label classification and more particularly to contradiction avoided learning for multi-class multi-label classification. Conventional classification methods do not consider contradictory outcomes in multi-label classification tasks wherein contradictory outcomes have significant negative impact in the classification problem solution. The present disclosure provides a contradiction avoided learning multi-class multi-label classification. The disclosed method utilizes a binary contradiction matrix constructed using domain knowledge. Based on the binary contradiction matrix the training dataset is divided into two parts, one comprising contradictions and the second without contradictions. The classification model is trained using the divided datasets using a contradiction loss and a binary cross entropy loss to avoid contradictions during learning of the classification model. The disclosed method is used for electrocardiogram classification, shape classification and so on.

18 Claims, 2 Drawing Sheets

(58) Field of Classification Search
CPC ...... G06F 16/285; G06F 16/288; G06F 16/35; G06F 16/353; G06F 17/16; G16H 50/70
See application file for complete search history.

(56) References Cited

U.S. PATENT DOCUMENTS

| | | | |
|---|---|---|---|
| 2020/0160177 A1* | 5/2020 | Durand | G06N 5/04 |
| 2021/0150316 A1* | 5/2021 | Riemenschneider | G06V 10/764 |
| 2021/0232966 A1 | 7/2021 | Elisha et al. | |
| 2021/0342453 A1* | 11/2021 | Leino | G06F 21/60 |
| 2021/0365743 A1* | 11/2021 | Sang | G06V 40/10 |
| 2022/0028063 A1 | 1/2022 | Guendel et al. | |

OTHER PUBLICATIONS

Hendycks et al., "Using Trusted Data to Train Deep Networks on Labels Corrupted by Severe Noise," (2019), pp. 1-17.

\* cited by examiner

METHOD AND SYSTEM FOR CONTRADICTION AVOIDED LEARNING FOR MULTI-CLASS MULTI-LABEL CLASSIFICATION

PRIORITY CLAIM

This U.S. patent application claims priority under 35 U.S.C. § 119 to: Indian Patent Application No. 202221062230, filed on Nov. 1, 2022. The entire contents of the aforementioned application are incorporated herein by reference.

TECHNICAL FIELD

The disclosure herein generally relates to multi-class multi-label classification, and, more particularly, to method and system for contradiction avoided learning for a multi-class multi-label classification.

BACKGROUND

Big data and deep learning methods are applied to a wide array of problems, and they provide good results for several technical problems. However, these methods are highly reliant on high quality labeled data in vast quantities. In highly technical and demanding domains, high quality labels are often hard to obtain, and extremely expensive. Thus, datasets used in practice are often noisy.

In a multi-label classification problem multiple classes may be present simultaneously which makes classification challenging. However, here an additional challenge is encountered if semantic information, or domain specific knowledge is not incorporated. For instance, in a medical context hyper-tension and hypo-tension may be predicted simultaneously. These sorts of logical errors get worse when the training dataset is noisy. In real life example of ECG classification, Atrial Fibrillation and Normal Sinus Rhythm condition cannot co-exist together. In multi-label classification tasks, the mutual exclusivity of class labels does not exist, which in turn, may result into classifying into labels which are contradictory in logical, domain-expert or other reliable source domains. Such outcomes from a classifier is unacceptable from a domain expert point of view, as not only do they make the system inaccurate, but shows a lack of understanding of the foundational aspects of the problem in question.

SUMMARY

Embodiments of the present disclosure present technological improvements as solutions to one or more of the above-mentioned technical problems recognized by the inventors in conventional systems. For example, in one embodiment, a method for contradiction avoided learning for multi-class multi-label classification is provided. The method includes: receiving a plurality of data instances and a plurality of user generated multi-label class labels, wherein each of the plurality of user generated multi-label class labels is associated with each data instance of the plurality of data instances; constructing a binary contradiction matrix based on a domain knowledge using the plurality of user generated multi-label class labels, wherein a distinct pair of user generated multi-label class labels in the binary contradiction matrix comprising at least one of (i) a value of 1 indicating contradiction and (ii) a value of 0 indicating no contradiction; splitting the plurality of data instances based on the constructed binary contradiction matrix into one of a first set of data instances and a second set of data instances; training a multi-label classification model using: the first set of data instances and the user generated multi-label class labels associated therewith based on a contradiction loss, and the second set of data instances and the user generated multi-label class labels associated therewith based on the contradiction loss and a binary cross entropy loss; generating a set of generated labels for each data instance using the trained multi-label classification model; and validating the trained multi-label classification model using the set of generated labels and the set of user generated multi-label class labels.

In another aspect, a system for contradiction avoided learning for multi-class multi-label classification is provided. The system comprises memory storing instructions; one or more communication interfaces; and one or more hardware processors coupled to the memory via the one or more communication interfaces, wherein the one or more hardware processors are configured by the instructions to receive a plurality of data instances and a plurality of user generated multi-label class labels, wherein each of the plurality of user generated multi-label class labels is associated with each data instance of the plurality of data instances; construct a binary contradiction matrix based on a domain knowledge using the plurality of user generated multi-label class labels, wherein a distinct pair of user generated multi-label class labels in the binary contradiction matrix comprising at least one of (i) a value of 1 indicating contradiction and (ii) a value of 0 indicating no contradiction; split the plurality of data instances based on the constructed binary contradiction matrix into one of a first set of data instances and a second set of data instances; train a multi-label classification model using: the first set of data instances and the user generated multi-label class labels associated therewith based on a contradiction loss, and the second set of data instances and the user generated multi-label class labels associated therewith based on the contradiction loss and a binary cross entropy loss; generate a set of generated labels for each data instance using the trained multi-label classification model; and validating the trained multi-label classification model using the set of generated labels and the set of user generated multi-label class labels.

In an embodiment, wherein the distinct pair of user generated multi-label class label in the contradiction matrix comprising the value of 1 is indicated as being logically inconsistent.

In an embodiment, wherein the first set of data instances comprising distinct pairs of user generated multi-label class labels associated with distinct pairs of the first set of data instances indicates as contradiction.

In an embodiment, wherein the second set of data instances comprising distinct pairs of user generated multi-label class labels associated with distinct pairs of the second set of data instances indicates as no contradiction.

In an embodiment, further comprising calculating number of contradictions from the set of generated labels wherein the number of contradictions is represented by $$\text{Number of contradictions} = \tfrac{1}{2} x^T C x$$

where x is the generated label, C is the binary contradiction matrix, T is the matrix transpose operator.

In an embodiment, wherein the contradiction loss is represented by $$\mathcal{L}' = x^T \cdot C \cdot \text{one-hot}(\text{argmax}(x))$$

where x is the generated label, C is the binary contradiction matrix, T is matrix transpose operator and $\mathcal{L}'$ is the contradiction loss.

In yet another aspect, there is provided a computer program product comprising a non-transitory computer readable medium having a computer readable program embodied therein, wherein the computer readable program, when executed on a computing device causes the computing device for contradiction avoided learning for multi-class multi-label classification by receiving a plurality of data instances and a plurality of user generated multi-label class labels, wherein each of the plurality of user generated multi-label class labels is associated with each data instance of the plurality of data instances; constructing a binary contradiction matrix based on a domain knowledge using the plurality of user generated multi-label class labels, wherein a distinct pair of user generated multi-label class labels in the binary contradiction matrix comprising at least one of (i) a value of 1 indicating contradiction and (ii) a value of 0 indicating no contradiction; splitting the plurality of data instances based on the constructed binary contradiction matrix into one of a first set of data instances and a second set of data instances; training a multi-label classification model using: the first set of data instances and the user generated multi-label class labels associated therewith based on a contradiction loss, and the second set of data instances and the user generated multi-label class labels associated therewith based on the contradiction loss and a binary cross entropy loss; generating a set of generated labels for each data instance using the trained multi-label classification model; and validating the trained multi-label classification model using the set of generated labels and the set of user generated multi-label class labels.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

In a multi-class multi-label classification training dataset is noisy. Classification performed in a noisy domain, often results in contradictory labels as outputs. The disclosed method improves learning in a noisy environment which in effect predicts contradiction-free outcomes. The classifier is learnt with the condition of minimization of contradiction loss, where the contradiction condition is derived from logical, expert-domain or other reliable sources. The embodiments of the present disclosure are described using multi-class multi-label electrocardiogram (ECG) classification problem, however, the approach is generic enough to incorporate similar type of classification problems.

Figure 1:
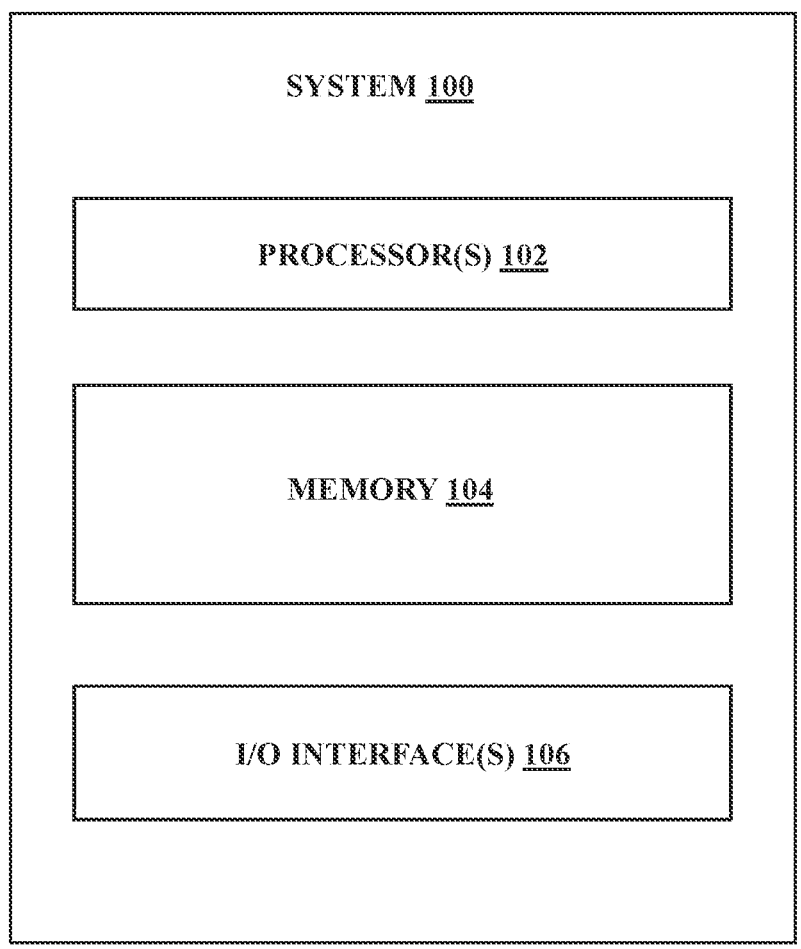
FIG. 1 illustrates an exemplary block diagram of a system for contradiction avoided learning for multi-class multi-label classification according to some embodiments of the present disclosure.
Figure 2:
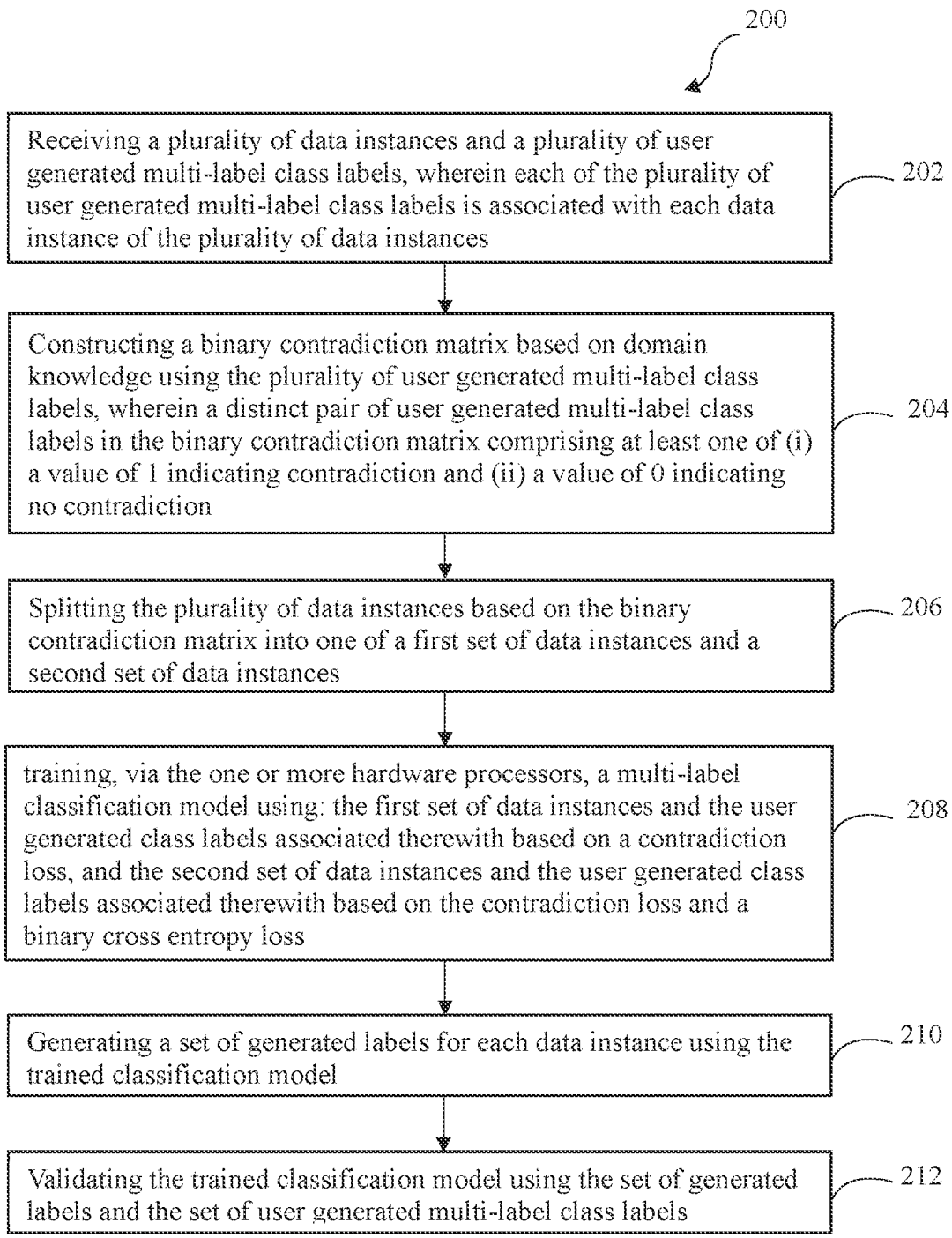
FIG. 2 is an exemplary flow diagram illustrating steps of method for contradiction avoided learning for multi-class multi-label classification according to some embodiments of the present disclosure.

Referring now to the drawings, and more particularly to FIG. 1 through FIG. 2, where similar reference characters denote corresponding features consistently throughout the figures, there are shown preferred embodiments and these embodiments are described in the context of the following exemplary system and/or method.

FIG. 1 illustrates a system 100 for contradiction avoided learning for multi-class multi-label classification. In an embodiment, the system 100 includes one or more processors 102, communication interface device(s) or input/output (I/O) interface(s) 106, and one or more data storage devices or memory 104 operatively coupled to the one or more processors 102. The memory 104 comprises one or more modules 108. The one or more processors 102 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface (s) 106 may include a variety of software and hardware interfaces, for example, a web interface, a graphical user interface, and the like and can facilitate multiple communications within a wide variety of networks and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a module for contradiction avoided learning for a multi-class multi-label classification of the system 100 along with a plurality of modules (not shown) to perform the methodology described herein.

FIG. 2 is an exemplary flow diagram illustrating steps of method for contradiction avoided learning for multi-class multi-label classification according to some embodiments of the present disclosure.

In an embodiment of the present disclosure, the one or more processors 102 are configured to receive at step 202, a plurality of data instances and a plurality of user generated multi-label class labels, wherein each of the plurality of user generated multi-label class labels is associated with each data instance of the plurality of data instances. For example, consider a dataset $D=\{(x_i, y_i)|i=\{1, \ldots N\}\}$ where for every data instance $x_i$ a ground truth label or a user generated label is provided represented as $y_i=\{A_1, \ldots A_k\}$. Such that $\{A_1, \ldots A_k\}$ is a set of class names stating that $x_i$ is an instance of type $A_j$.

In an embodiment of the present disclosure, the one or more processors 102 are configured to construct at step 204, a binary contradiction matrix based on a domain knowledge using the plurality of user generated multi-label class labels, wherein a distinct pair of user generated multi-label class labels in the binary contradiction matrix comprising at least one of (i) a value of 1 indicating contradiction and (ii) a value of 0 indicating no contradiction. The binary contradiction matrix is constructed with consultation of related domain-experts or related domain-knowledge. The domain knowledge often qualitative is quantified to form the binary contradiction matrix by domain experts or by using techniques such as natural language processing techniques. The NLP techniques is applied to the related domain literature to form the binary contradiction matrix. The distinct pair of user generated multi-label class label in the contradiction matrix comprising the value of 1 is indicated as being logically inconsistent. The Table 1 shows the binary contradiction matrix for electrocardiogram (ECG) classification from Physionet 2022 dataset. In real life example of ECG classification, Atrial Fibrillation and Normal Sinus Rhythm condition cannot co-exist together. The construction of the binary contradiction matrix is performed typically with the knowledge from domain experts. For example, the binary contradiction matrix is formed through series of discussion with a cardiologist and referring relevant literature on ECG. The formed binary contradiction matrix is further ratified by the cardiologist. Mostly domain experts have qualitative understanding of the contradiction. The knowledge is quantified in the binary contradiction matrix with binary inputs 1 or 0, where 1 represents a no contradiction and 0 represents a contradiction. If there are total N classes present, N×N binary contradiction matrix is constructed. Table 1 illustrates an example of a binary contradiction matrix for ECG classification for contradiction avoided learning for multi-class multi-label classification according to some embodiments of the present disclosure.

TABLE 1

| | IAVB | AF | AFL | Brady | CRBBB | IRBBB | LAnFB | LAD | LBB | LQRSV | NSIVCB | PR | PAC | PVC | LPR | LQT | QAb | RAD | SA | SB | STach | TAb | TInv | NSR |
|---|---|---|---|---|---|---|---|---|---|---|---|---|---|---|---|---|---|---|---|---|---|---|---|---|
| IAVB | | | | | | | | | | | | | | | | | | | | | | | | 1 |
| AF | | | | | | | | | | | | 1 | 1 | | 1 | | | | 1 | 1 | 1 | | | 1 |
| AFL | | | | | | | | | | | | 1 | 1 | | 1 | | | | 1 | 1 | 1 | | | 1 |
| Braddy | | | | | | | | | | | | | | | | | | | | | 1 | | | 1 |
| CRBBB | | | | | | | | | | | | 1 | | | | | | | | | | | | 1 |
| IRBBB | | | | | | | | | | | | 1 | | | | | | | | | | | | 1 |
| LAnFB | | | | | | | | | | | | 1 | | | | | | | | | | | | 1 |
| LAD | | | | | | | | | | | | | | | | | | | | | | | | 1 |
| LBB | | | | | | | | | | | | | | | | | | | | | | | | 1 |
| LQRSV | | | | | | | | | | | | | | | | | | | | | | | | |
| NSIVCB | | | | | | | | | | | | | | | | | | | | | | | | 1 |
| PR | | 1 | 1 | | 1 | | 1 | 1 | | | | | | | | | | | 1 | 1 | 1 | | | |
| PAC | | 1 | 1 | | | | | | | | | | | | | | | | | | | | | 1 |
| PVC | | | | | | | | | | | | | | | | | | | | | | | | 1 |
| LPR | | 1 | 1 | | | | | | | | | | | | | | | | | | | | | 1 |
| LQT | | | | | | | | | | | | | | | | | | | | | | | | 1 |
| QAb | | | | | | | | | | | | | | | | | | | | | | | | 1 |
| RAD | | | | | | | | | | | | | | | | | | | | | | | | 1 |
| SA | | 1 | 1 | | | | | | | | | 1 | | | | | | | | | | | | 1 |
| SB | | 1 | 1 | | | | | | | | | 1 | | | | | | | | | 1 | | | 1 |
| STach | | 1 | 1 | 1 | | | | | | | | | | | | | | | | | | | | |
| TAb | | | | | | | | | | | | | | | | | | | | | | | | |
| TInv | | | | | | | | | | | | | | | | | | | | | | | | |
| NSR | | | | | | | | | | | | | | | | | | | | | | | | |

TABLE 1-continued

| | | | |
|---|---|---|---|
| STach | 1 | 1 | 1 |
| TAb | | | 1 |
| TInv | | | 1 |
| NSR | | | 1 |

In an embodiment of the present disclosure, the one or more processors 102 are configured to split at step 206, the plurality of data instances based on the constructed binary contradiction matrix into one of a first set of data instances and a second set of data instances. The annotated labels of the plurality of data instances are checked in the binary contradiction matrix and if at least one of the labels are contradictory, it is identified as a contradictory data instance. The step 206 involves splitting the plurality of data instances into two parts wherein one part involving the first set of data instances containing contradictions (D') which occur due to inaccurate labeling and the second part involving the second set of data instances containing without contradictions (D*). The first set of data instances comprising distinct pairs of user generated multi-label class labels associated with distinct pairs of the first set of data instances indicates as contradiction. the second set of data instances comprising distinct pairs of user generated multi-label class labels associated with distinct pairs of the second set of data instances indicates as no contradiction.

In an embodiment of the present disclosure, the one or more processors 102 are configured to train at step 208, a multi-label classification model using: the first set of data instances and the user generated multi-label class labels associated therewith based on a contradiction loss, and the second set of data instances and the user generated multi-label class labels associated therewith based on the contradiction loss and a binary cross entropy loss. The multi-label classification model is trained using the first set of data instances based on the contradiction loss. The contradiction loss is represented as $$\mathcal{L}' = x^T \cdot C \cdot \text{one-hot}(\text{argmax}(x)) \quad (1)$$

where x is a generated label (output from the multi-label classification model), C is the binary contradiction matrix, T is matrix transpose operator and $\mathcal{L}'$ is the contradiction loss. Minimizing the contradiction loss means the multi-label classification model learns to avoid contradictory predictions.

The multi-label classification model is trained using the second set of data instances based on the contradiction loss and the binary cross entropy loss. The contradiction loss and the binary cross entropy loss is represented as $$\mathcal{L} = \Sigma_i(\hat{y}_i \log(x_i) + (1-\hat{y}_i)\log(1-x_i)) + \mu(x^T \cdot C \cdot \text{one-hot}(\text{argmax}(x))) \quad (2)$$

where $\mu$ is a constant deciding the balance between the binary cross entropy loss and the contradiction loss, x is the generated label (output from the multi-label classification model) $\hat{y}_i$ is the user generated class label (ground truth) and C is the binary contradiction matrix. The number of contradictions from the set of generated labels which forms as an indicator variable is calculated and represented by $$\text{Number of contradictions} = \frac{1}{2} x^T C x \quad (3)$$

where x is the generated label, C is the binary contradiction matrix, T is the matrix transpose operator.

In an embodiment of the present disclosure, the one or more processors 102 are configured to generate at step 210, a set of generated labels for each data instance using the trained multi-label classification model.

In an embodiment of the present disclosure, the one or more processors 102 are configured to validate at step 212, the trained multi-label classification model using the set of generated labels and the set of user generated multi-label class labels.

EXPERIMENTAL RESULTS: Experiments for the disclosed method were performed using the Physionet 2020/21 dataset and showed similar patterns. In multi-class multi-label classification problem, the objective is not only to have higher accuracy, F1 score or challenge metric, but also to have better contradiction, hamming loss and coverage metrics.

Coverage represents on average how far down the ranked list must be traversed, to get every label. It is the least number of predictions to make the right prediction. (minimum=average number of labels, smaller is better). Hamming Loss represents average number of missed labels and over-diagnosis of labels, (minimum=0, smaller is better)

Table 2 provides a comparison of performance of raw sampling technique, contradiction avoided sampling technique (CAS) and contradiction avoided sampling with contradiction loss technique (CAS+Loss). In multi-class multi-label classification problem, the objective is not only to have higher accuracy, F1 score or challenge metric (CM), but also to have better contradiction, hamming loss and coverage metrics. In Table 2 it is seen that the CAS+Loss has high CM, high F1 score, high accuracy, low contradiction, low hamming loss and low coverage which shows that the disclosed method gives a higher performance than the compared techniques.

TABLE 2

| | Raw | CAS | CAS + Loss |
|---|---|---|---|
| Train CM | 0.596 | 0.685 | 0.701 |
| Test CM | 0.587 | 0.615 | 0.642 |
| F1 | 0.436 | 0.498 | 0.513 |
| Accuracy | 42.31 | 56.53 | 56.98 |
| Contradiction | 0.672 | 0.086 | 0.010 |
| Hamming loss | 2.298 | 0.978 | 1.007 |
| Coverage (expected) | 0.971 | 1.155 | 1.060 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of the disclosed method provides a method for contradiction avoided learning for multi-class multi-label classification. The method utilizes a binary contradiction matrix which is constructed using the domain knowledge. The training dataset is divided into two parts based on the binary contradiction matrix. One part comprises contradictions and the other part comprises without contradictions training data. These divided datasets are used for training a classification model using a contradiction loss and a binary cross entropy loss to avoid contradictions during the learning process of the classification model.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:
receiving, via one or more hardware processors, a plurality of data instances and a plurality of user generated multi-label class labels, wherein each of the plurality of user generated multi-label class labels is associated with each data instance of the plurality of data instances;
constructing, via the one or more hardware processors, a binary contradiction matrix based on a domain knowledge using the plurality of user generated multi-label class labels, wherein a distinct pair of user generated multi-label class labels in the binary contradiction matrix comprising at least one of (i) a value of 1 indicating contradiction and (ii) a value of 0 indicating no contradiction;
splitting, via the one or more hardware processors, the plurality of data instances based on the constructed binary contradiction matrix into one of a first set of data instances and a second set of data instances;
training, via the one or more hardware processors, a multi-label classification model using:
the first set of data instances and the user generated class labels associated therewith based on a contradiction loss, and
the second set of data instances and the user generated class labels associated therewith based on the contradiction loss and a binary cross entropy loss;
generating, via the one or more hardware processors, a set of generated labels for each data instance using the trained classification model; and
validating, via the one or more hardware processors, the trained multi-label classification model using the set of generated labels and the set of user generated multi-label class labels.

2. The method of claim 1, wherein the distinct pair of user generated multi-label class label in the contradiction matrix comprising the value of 1 is indicated as being logically inconsistent.

3. The method of claim 1, wherein the first set of data instances comprising distinct pairs of user generated multi-label class labels associated with distinct pairs of the first set of data instances indicates as contradiction.

4. The method of claim 1, wherein the second set of data instances comprising distinct pairs of user generated multi-label class labels associated with distinct pairs of the second set of data instances indicates as no contradiction.

5. The method of claim 1, further comprising calculating number of contradictions from the set of generated labels wherein the number of contradictions is represented by:

Number of contradictions=$\frac{1}{2}x^T C x$ wherein x is the generated label, C is the binary contradiction matrix, T is the matrix transpose operator.

6. The method of claim 1, wherein the contradiction loss is represented by:

$$\mathcal{L}'=x^T \cdot C \cdot \text{one-hot}(\text{argmax}(x))$$

wherein x is the generated label, C is the binary contradiction matrix, T is matrix transpose operator and $\mathcal{L}'$ is the contradiction loss.

7. A system, comprising:
a memory storing instructions;
one or more communication interfaces; and
one or more hardware processors coupled to the memory via the one or more communication interfaces, wherein the one or more hardware processors are configured by the instructions to:
receive a plurality of data instances and a plurality of user generated multi-label class labels, wherein each of the plurality of user generated multi-label class labels is associated with each data instance of the plurality of data instances;
construct a binary contradiction matrix based on a domain knowledge using the plurality of user generated multi-label class labels, wherein a distinct pair of user generated multi-label class labels in the binary contradiction matrix comprising at least one of (i) a value of 1 indicating contradiction and (ii) a value of 0 indicating no contradiction;
split the plurality of data instances based on the constructed binary contradiction matrix into one of a first set of data instances and a second set of data instances;
train a multi-label classification model using:
the first set of data instances and the user generated multi-label class labels associated therewith based on a contradiction loss, and
the second set of data instances and the user generated multi-label class labels associated therewith based on the contradiction loss and a binary cross entropy loss;
generate a set of generated labels for each data instance using the trained multi-label classification model; and
validate the trained multi-label classification model using the set of generated labels and the set of user generated multi-label class labels.

8. The system of claim 7, wherein the distinct pair of user generated multi-label class label in the contradiction matrix comprising the value of 1 is indicated as being logically inconsistent.

9. The system of claim 7, wherein the first set of data instances comprising distinct pairs of user generated multi-label class labels associated with distinct pairs of the first set of data instances indicates as contradiction.

10. The system of claim 7, wherein the second set of data instances comprising distinct pairs of user generated multi-label class labels associated with distinct pairs of the second set of data instances indicates as no contradiction.

11. The system of claim 7, further comprising calculating number of contradictions from the set of generated labels wherein the number of contradictions is represented by:

$$\text{Number of contradictions}=\frac{1}{2}x^T C x$$

wherein x is the generated label, C is the binary contradiction matrix, T is the matrix transpose operator.

12. The system of claim 7, wherein the contradiction loss is represented by $$\mathcal{L}'=x^T \cdot C \cdot \text{one-hot}(\text{argmax}(x))$$

where x is the generated label, C is the binary contradiction matrix, T is matrix transpose operator an $\mathcal{L}'$ is the contradiction loss.

13. One or more non-transitory machine-readable information storage mediums comprising one or more instructions which when executed by one or more hardware processors cause:
receiving, a plurality of data instances and a plurality of user generated multi-label class labels, wherein each of the plurality of user generated multi-label class labels is associated with each data instance of the plurality of data instances;
constructing a binary contradiction matrix based on a domain knowledge using the plurality of user generated multi-label class labels, wherein a distinct pair of user generated multi-label class labels in the binary contradiction matrix further comprising at least one of (i) a value of 1 indicating contradiction and (ii) a value of 0 indicating no contradiction;
splitting the plurality of data instances based on the constructed binary contradiction matrix into one of a first set of data instances and a second set of data instances;
training a multi-label classification model using:
the first set of data instances and the user generated multi-label class labels associated therewith based on a contradiction loss, and
the second set of data instances and the user generated multi-label class labels associated therewith based on the contradiction loss and a binary cross entropy loss;
generating a set of generated labels for each data instance using the trained multi-label classification model; and
validating the trained multi-label classification model using the set of generated labels and the set of user generated multi-label class labels.

14. The one or more non-transitory machine-readable information storage mediums of claim 13, wherein the one or more instructions which when executed by the one or more hardware processors further cause the value of 1 is indicated as being logically inconsistent.

15. The one or more non-transitory machine-readable information storage mediums of claim 13, wherein the one or more instructions which when executed by the one or more hardware processors further cause distinct pairs of user generated multi-label class labels associated with distinct pairs of the first set of data instances indicates as contradiction.

16. The one or more non-transitory machine-readable information storage mediums of claim 13, wherein the one or more instructions which when executed by the one or more hardware processors further cause distinct pairs of user generated multi-label class labels associated with distinct pairs of the second set of data instances indicates as no contradiction.

17. The one or more non-transitory machine-readable information storage mediums of claim 13, wherein the one or more instructions which when executed by the one or more hardware processors further cause calculating number of contradictions from the set of generated labels wherein the number of contradictions is represented by:

$$\text{Number of contradictions}=\frac{1}{2}x^T C x$$

wherein x is the generated label, C is the binary contradiction matrix, T is the matrix transpose operator.

18. The one or more non-transitory machine-readable information storage mediums of claim 13, wherein the contradiction loss is represented by:

$$\mathcal{L}' = x^T \cdot C \cdot \text{one-hot}(\text{argmax}(x))$$

wherein x is the generated label, C is the binary contradiction matrix, T is matrix transpose operator and $\mathcal{L}'$ is the contradiction loss.

* * * * *